United States Patent [19]
Adair

[11] Patent Number: 5,494,483
[45] Date of Patent: Feb. 27, 1996

[54] STEREOSCOPIC ENDOSCOPE WITH MINIATURIZED ELECTRONIC IMAGING CHIP

[76] Inventor: Edwin L. Adair, 317 Paragon Way, Castle Pines Village, Colo. 80104

[21] Appl. No.: 330,426

[22] Filed: Oct. 28, 1994

Related U.S. Application Data

[62] Division of Ser. No. 954,578, Sep. 30, 1992, Pat. No. 5,381,284.

[51] Int. Cl.$^6$ .............................. A61B 1/04; H04N 7/18
[52] U.S. Cl. ........................ 600/111; 600/130; 600/129; 348/45
[58] Field of Search .................................. 600/110, 111, 600/130, 166, 173, 176; 348/45–47, 65, 68; 257/53, 59, 98, 447, 448, 228, 464

[56] References Cited

U.S. PATENT DOCUMENTS

| | | |
|---|---|---|
| 3,520,587 | 7/1970 | Tasaki et al. . |
| 4,786,965 | 11/1988 | Yabe ........................ 600/130 |
| 4,862,873 | 9/1989 | Yajima et al. . |
| 4,873,572 | 10/1989 | Miyazaki et al. .................... 358/98 |
| 4,895,431 | 1/1990 | Tsujiuchi et al. . |
| 4,924,853 | 5/1990 | Jones, Jr. et al. . |
| 4,926,257 | 5/1990 | Miyazaki . |
| 5,166,787 | 11/1992 | Irion ........................ 348/75 |
| 5,173,756 | 12/1992 | Wong et al. ............... 257/243 |
| 5,184,602 | 2/1993 | Anapliotis et al. ............. 600/176 |

*Primary Examiner*—Richard J. Apley
*Assistant Examiner*—John P. Leubecker
*Attorney, Agent, or Firm*—Fields, Lewis & Rost

[57] ABSTRACT

In accordance with one form of the present invention, a stereoscopic endoscope is provided which has an elongated thin cylindrical barrel with a pair of CCDs mounted transversely within the barrel adjacent the distal end thereof. A pair of objective optics are mounted within the barrel between the distal end thereof and the respective CCDs for focusing an image observed through the endoscope on the CCDs. Image signal transmitting wires connected to each CCD extend longitudinally through the barrel and out the proximal end thereof for transmitting an image signal to a remote location. Light transmitting fibers are tightly packed around the objective optics and the CCDs. A first connector is secured to the proximal end of the wires for connection to a stereoscopic image producing device and a second connector is secured to the proximal of the light transmitting fibers for connection to a light source. In another embodiment, the CCDs are mounted in back-to-back relationship and use a prism for directing and focusing an imaging on each CCD. In a third embodiment, an end cap is hinged to the distal end of the barrel with one CCD mounted at the end of the barrel and the other CCD mounted in the end of the end cap in face-to-face relationship with the first CCD when the end cap is closed. The end cap can be swung to an open position to generate a stereoscopic image.

9 Claims, 4 Drawing Sheets

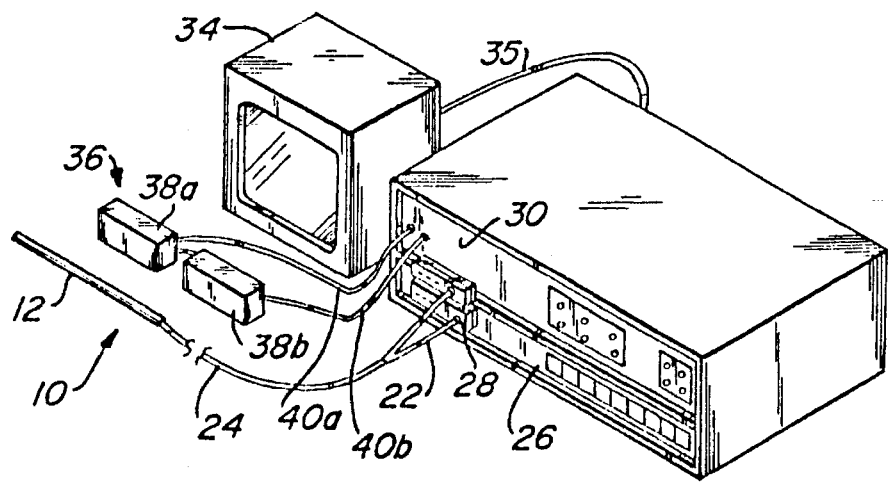
Fig_1
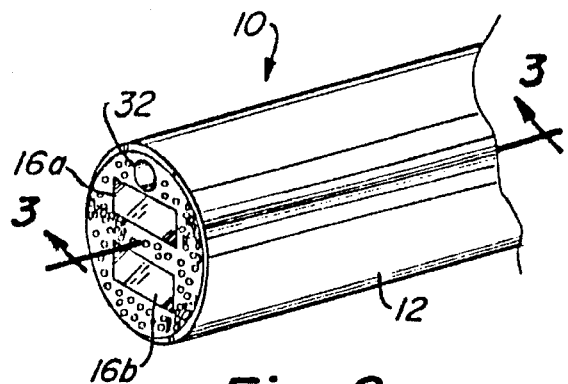
Fig_2
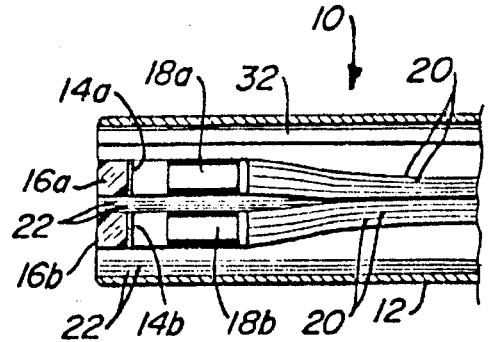
Fig_3
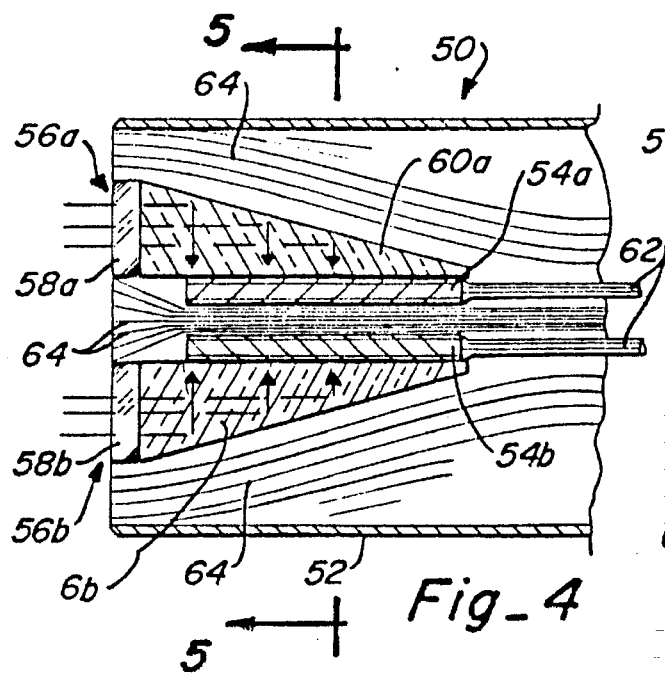
Fig_4
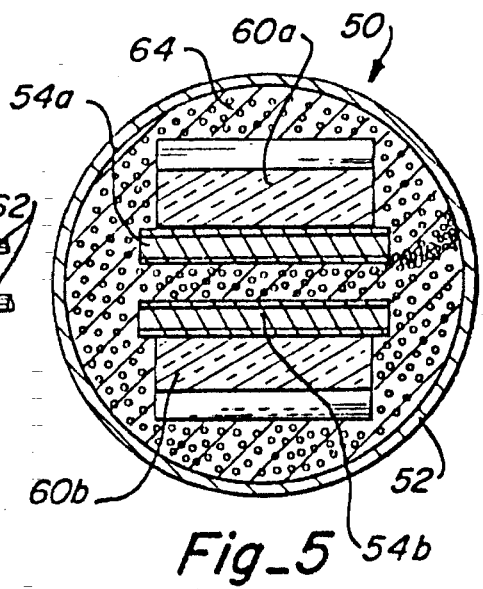
Fig_5

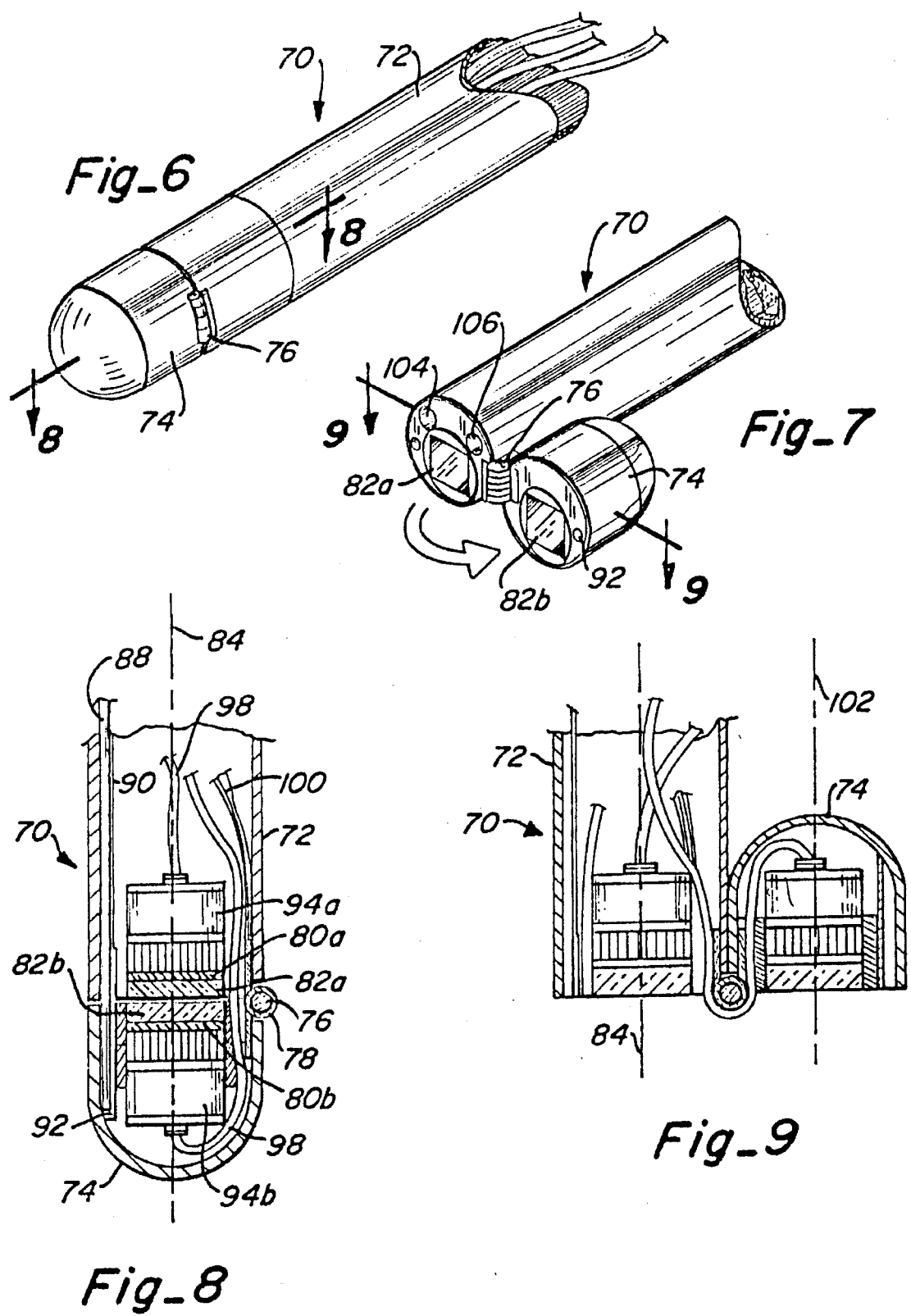

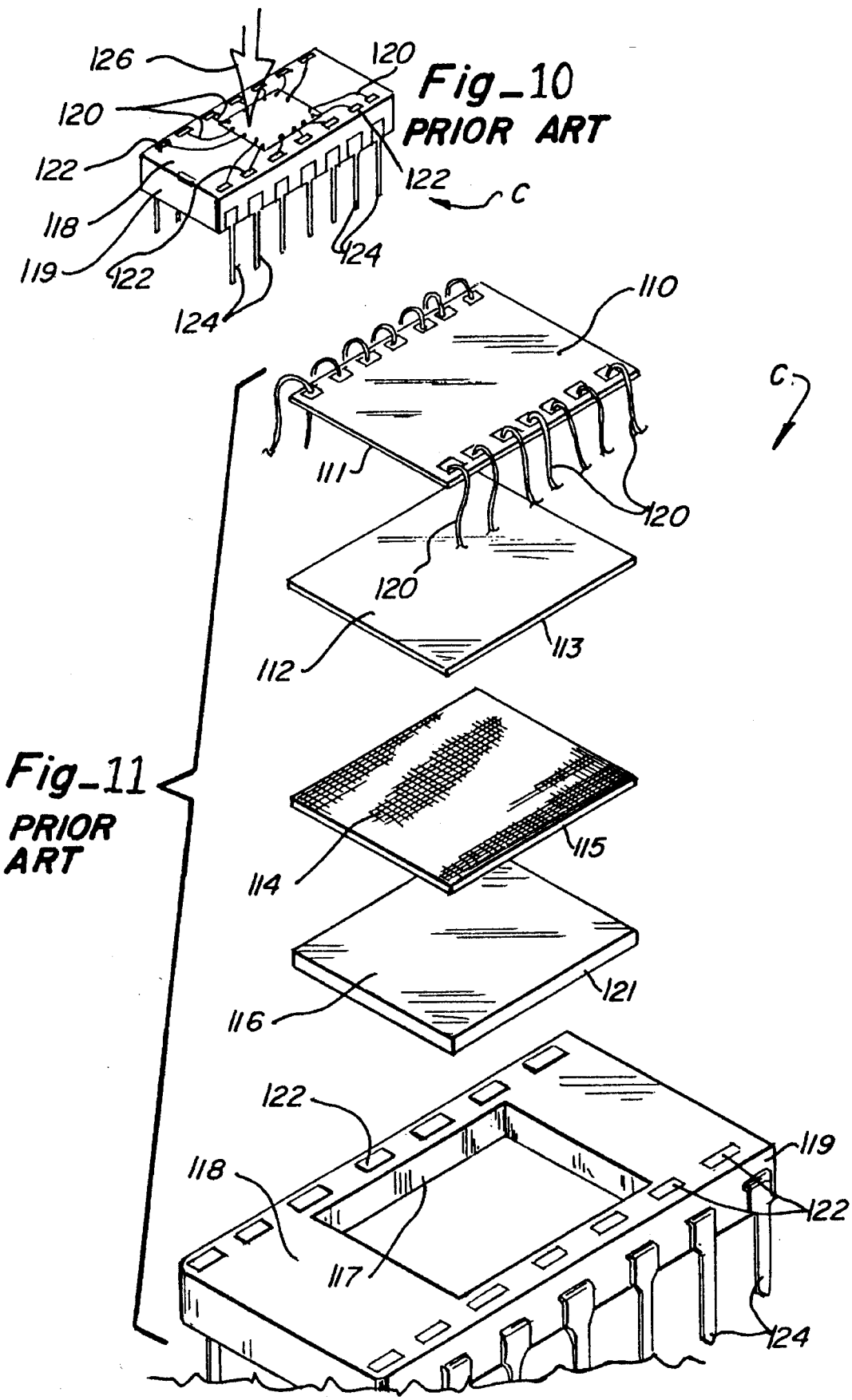

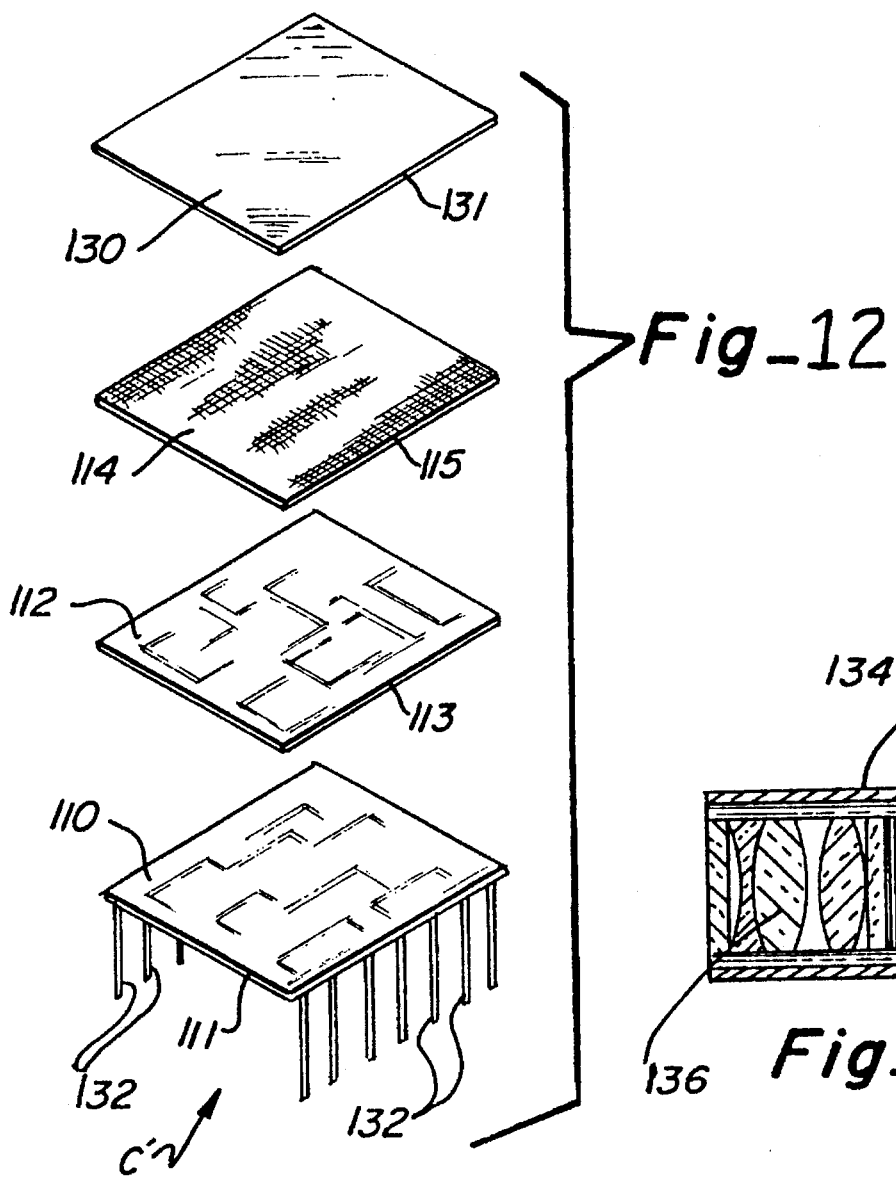
Fig_12
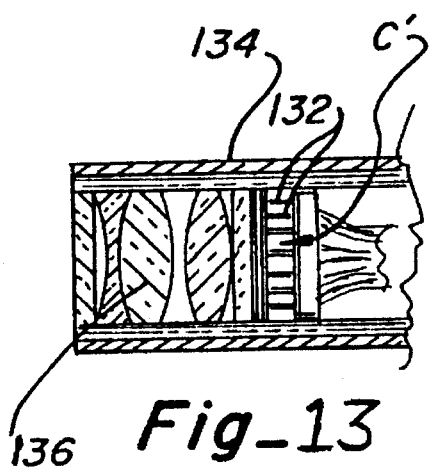
Fig_13

STEREOSCOPIC ENDOSCOPE WITH MINIATURIZED ELECTRONIC IMAGING CHIP

This is a division, of U.S. application Ser. No. 07/954,578 filed Sep. 30, 1992, now U.S. Pat. No. 5,381,284.

TECHNICAL FIELD

This invention relates to an endoscope and more particularly to a stereoscopic endoscope of small diameter.

BACKGROUND ART

Stereoscopic endoscopes are known in the prior art. However, they are very large and bulky and hard to use. Also, they include complicated optics which make them very expensive. Because of their size they can create great discomfort to the patient.

In spite of these difficulties, a small diameter stereoscopic endoscope would be desirable because it would give the doctor a three-dimensional view of the operative site. Such a three-dimensional view will greatly enhance the physician's ability to evaluate conditions at the operative site and to successfully manipulate operative devices at the site to complete the desired operative procedure.

Examples of stereoscopic endoscopes are as follows:

Tasaki et al., U.S. Pat. No. 3,520,587, discloses a stereoscopic endoscope having two flexible fiber optic systems with objective lens systems being located at the distal end of each for focusing an image of the site to be inspected. An ocular is located at the proximal end of each fiber bundle for viewing the transmitted images. A visual perception in three-dimension is thereby created. This device is intended to provide a stereoscopic endoscope of limited diameter, but because of the use of light fibers for both transmitting and receiving light and the requirement for relatively sophisticated electronics, the device is still larger than desired and quite costly.

Miyazaki, U.S. Pat. No. 4,926,257, discloses a stereoscopic endoscope comprising a single solid-state image sensor and an optical image system. Stereoscopic imaging is made possible by shifting the solid-state image sensor back and forth between the two optical imaging systems. A prism system is provided in which images are sequentially transmitted to provide the three-dimensional image for viewing.

Jones, Jr. et al., U.S. Pat. No. 4,924,853, also discloses a stereoscopic endoscope using a single imaging lens whereby the image is split by a split beam prism, which images are converted to electrical signals and displayed on a television screen. The images are transmitted from the lens by means of coherent light transmitting elements. This device also provides for the alternate transmission of images to provide a three-dimensional image for viewing.

Yajima et al., U.S. Pat. No. 4,862,873, discloses a stereoscopic endoscope comprising a pair of optical guides which are capable of conducting and illuminating light to be reflected on the site to be observed. While one optical guide conducts the illuminating light, the other optical guide conducts the light from the object being observed. The optical guides can be switched from one function to the other, thereby creating a stereoscopic image.

Tsujiuchi et al., U.S. Pat. No. 4,895,431, discloses a stereoscopic endoscope in which a first endoscope image is taken at one position while a second endoscopic image is taken from a second position. The endoscopic images are partially overlapped with means for detecting the relationship between the first and second images, thereby providing a three-dimensional image.

Each of the devices described above, is complex and therefor expensive. Also, none of them provide an endoscope in which two CCDs are in transverse side-by-side relationship within the endoscope, thereby adding to their complexity and/or size.

DISCLOSURE OF THE INVENTION

In accordance with one form of the present invention, a stereoscopic endoscope is provided which has an elongated thin cylindrical barrel, a distal end and a proximal end. A pair of charge coupled devices, also known as CCDs, are mounted in spaced relationship within the barrel adjacent the distal end thereof. A pair of objective optics are mounted within the barrel between the distal end thereof and the respective CCDs. The objective optics are each coterminous with the distal end of the barrel for focusing an image observed through the endoscope on the CCDs. Image signal transmitting wires connected to each CCD extend longitudinally through the barrel and out the proximal end thereof for transmitting an image signal to a remote location. Light transmitting fibers are positioned around the objective optics and the CCDs and have distal ends coterminous with the distal end of the barrel. A first connector is secured to the proximal end of the wires for connection to a stereoscopic image producing device and a second connector is secured to the proximal of the light transmitting fibers for connection to a light source.

In another embodiment, the CCDs are mounted in back-to-back relationship and the objective optics each include a prism for directing and focusing an imaging on each CCD.

In a third embodiment, an end cap is hinged to the distal end of the barrel with one CCD mounted at the end of the barrel and the other CCD mounted in the end of the end cap in face-to-face relationship with he first CCD when the end cap is closed. The end cap can be swung to an open position to generate a stereoscopic image. The objective optics for the second CCD are mounted in the end cap in front of the CCD. The image signal transmitting wires for the second CCD pass from the end cap past the hinge and longitudinally through the barrel. Conveniently, the light transmitting fibers are tightly packed around the objective optics and the CCDs.

The hinged version of the device can include a coil spring around the hinge which normally urges the end cap toward the open position. Conveniently, a channel can extend longitudinally through the barrel and a sleeve can be provided in the end cap which is aligned with the channel when the end cap is closed position. A locking rod is then extendable through the channel and has a distal end receivable in frictional engagement with the sleeve to hold the end cap in closed position against the force of the spring. After the endoscope has been inserted into the patient's body, the locking rod can be withdrawn which then releases the end cap to be swung by the force of the spring to its open position.

The CCDs are of a miniaturized electronic imaging chip interline transfer architecture. The CCDs comprise stratified layers wherein a base silicon layer is thin enough to allow passage therethrough of most UV, visible and IR light which strikes a pixel layer formed on the back side of the base silicon layer. Various interconnect layers including an interlace circuit, vertical shift register, horizontal shift register and an output register are terminated on the chip margins on the surface of the outermost interconnect layer as bonding site pads to allow bump bonding of electrical pins extending away from the chip for attachment to means for sensing electrical signals generated by an image projected onto the pixel layer through the base silicon layer. Preferably, the leads are bonded perpendicular to the chip surface and lie within an area defined by the peripheral edge of the silicon layer.

The manufacturing process used to make these CCDs begins with shaving the silicon substrate on the back side of a standard CCD to a sufficient thinness to allow passage of a light image therethrough. The CCD is then reversed so that the image is projected through the thin back side of the silicon substrate. Leads are bumped bond to the former front surface of the CCD in perpendicular relation thereto so as to lie within the area defined by the peripheral edge thereof for supplying electrical signals to and from the CCD. These modifications significantly reduce the outside dimensions of the CCD architecture by totally eliminating the frame which supports the CCD and holds the standard electrical leads and required packaging.

By this process, a CCD is provided whose surface area is no greater than that defined by the pixel layer itself. Furthermore, the total thickness of the chip is reduced. This process makes the chip sufficiently small enabling it to be used in the invention disclosed herein.

From the foregoing, it can be seen that a stereoscopic endoscope has been provided which is of simple construction and small in size and in which the CCD devices can be placed in side-by-side relationship in a thin endoscope body.

Additional advantages of this invention will become apparent from the description which follows, taken in conjunction with the accompanying drawings.

BRIEF DESCRIPTION OF THE DRAWINGS

FIG. 1 is a perspective view of a stereoscopic endoscope of this invention connected to suitable light generating means and image processing means;

FIG. 2 is an enlarged fragmentary perspective view of the distal end of a stereoscopic endoscope constructed in accordance with this invention;

FIG. 3 is a horizontal section, taken along line 3—3 of FIG. 2, showing the internal components of the stereoscopic endoscope;

FIG. 4 is a greatly enlarged fragmentary section of the terminal end of an alternative embodiment of the stereoscopic endoscope wherein the CCDs are in back-to-back relationship;

FIG. 5 is a vertical section, taken along line 5—5 of FIG. 4, showing further details of this embodiment;

FIG. 6 is a perspective fragmentary view of an alternative embodiment with a hinged end cap in closed position;

FIG. 7 is a fragmentary perspective view, similar to FIG. 6 but showing the end cap in open position;

FIG. 8 is an enlarged fragmentary horizontal section, taken along line 8—8 of FIG. 6, showing further details of the endoscope; and FIG. 9 is an enlarged fragmentary horizontal section, taken along line 9—9 of FIG. 7, showing further details of the endoscope with the end cap in open position.

FIG. 10 is a perspective view of a prior art CCD supported in an opening in a large substrate which includes the electronic packaging;

FIG. 11 is an exploded, diagrammatical, enlarged view of the CCD of FIG. 1;

FIG. 12 is an exploded, diagrammatical view of a CCD constructed in accordance with this invention; and FIG. 13 is a section showing the CCD of FIG. 3 used with a lens system in an endoscope.

BEST MODE FOR CARRYING OUT THE INVENTION

In accordance with this invention, a stereoscopic endoscope 10 is provided, as shown in FIGS. 1–3 which has a thin elongated hollow barrel 12. A pair of imaging chips, such as CCDs 14a and 14b are mounted adjacent to the distal end of barrel 12 with objective optics 16a and 16b mounted between the distal end of barrel 12 and the CCDs for focusing an image of an investigative or operative site onto the CCDs. The CCDs are connected to suitable electronic packages 18a and 18b which in turn are connected to image signal transmitting wires 20 which extend longitudinally through the barrel and out the distal end thereof. Light transmitting fibers 22 extend longitudinally through barrel 12 and are tightly packed around and between the objective optics 16 and the CCDs 14a and 14b and extend longitudinally through the barrel and out the distal end. The wires 20 and light fibers 22 are contained within a sleeve 24 extending from the distal end of barrel 12, as seen in FIG. 1. The light fibers 22 exit the proximal end of sleeve 24 and are connected to a light source 26 by means of a connector 28 attached to the proximal end of light fibers 22. The light fibers are also coterminous with the distal end of barrel 12. The proximal end of wires 20 exit the proximal end of sleeve 24 and are connected to electronic control unit 30. Barrel 12 can also be provided with a longitudinal passageway or channel 32 to which a source of fluid can be connected for clearing the viewing area at the distal end of endoscope 10. Channel 32 also can be used for inserting operative instruments to conduct an operative procedure at the operative site.

The spacing between CCDs 14a and 14b provides the parallax needed to create a stereoscopic view. The CCDs 14a and 14b can be mounted at a slight angle of convergence, such as 1°, or they can be mounted parallel and utilize a software system to create the convergence electronically.

Although the CCDs have been illustrated in the drawings as one above the other, they may be located side-by-side. However, it has been found that the eyes and brain fuse the images from the CCDs better and provide a superior stereoscopic view for the physician when one CCD is above the other. However, either configuration is acceptable.

Control unit 30 contains two TV cameras video processing units which alternately provide images to TV monitor 34 through cable 35. A suitable control unit for this purpose is shown in U.S. Pat. No. 4,862,873 to Yajima et al., entitled "Stereo Endoscope". The structure and description of the control unit disclosed in this patent is hereby incorporated by reference. The image displayed on monitor 34 is imaged on the right eye or the left eye through shield glasses 36 having shield filters 38a and 38b which are connected to control unit 30 by means of cables 40a and 40b. Shield filters 38a and 38b can be liquid crystal shutters which utilize twistneumatic liquid crystal. When a voltage is applied to shield filter 38a, light is prevented from being transmitted therethrough to the eye of the physician. Conversely, at the same time no voltage will be applied to shield filter 38b allowing an image to pass therethrough to the other eye of the physician. The voltages will be applied and interrupted alternately through cables 40a and 40b. A rate, such as fifty cycles per second, is sufficiently fast so that the alternate interruption of the eyes is not apparent, so that the physician views a stereoscopic image on monitor 34 when viewing the monitor through shield glasses 36. It should be noted that other systems are available or under development utilizing multi-sync TV monitors and utilizing other liquid crystal members which can be used to provide display of stereoscopic images without the need for shield glasses.

It will be noted that the CCDs 14a and 14b are mounted transversely across the barrel 12 which arrangement has not been possible with prior stereoscopic endoscopes. It is possible with applicant's invention, because of the development of a new CCD shown incorporated by reference.

An alternative stereoscopic endoscope 50 is shown in FIGS. 4 and 5. This endoscope includes a barrel 52 in which the CCDs 54a and 54b are mounted centrally in back-to-back relationship. The objective optics 56a and 56b include objective lenses 58a and 58b, respectively, and prisms 60a and 60b, respectively, which focus and direct an image from an image site to CCDs 54a and 54b, respectively. CCDs are connected to image signal transmitting wires 62 which extend longitudinally through the barrel as in the previous embodiment. Light transmitting fibers 64 are packed tightly around the objective optics and CCDs and between them for transmitting light to the operative site. These fibers run longitudinally through barrel 52. The image signal transmitting wires 62 and light fibers 64 are connected at their proximal ends to an electronic control unit, such as control unit 30 in FIG. 1 and to a source of light, such as light source 26. The image is reproduced on a monitor such as monitor 34 and viewed through glasses such as shield glasses 36 in the manner previously described. With this arrangement, the diameter of barrel 52 may be even smaller than that of barrel 12 in the previous embodiment.

Although not shown, the embodiment of FIGS. 4 and 5 could be provided with a channel such as channel 32 shown in the embodiments of FIGS. 1–3, for the same purpose.

A still further embodiment is shown in FIGS. 6–9. In this embodiment, an endoscope 70 has a barrel 72. End cap 74 is pivotally attached to the distal end of barrel 72 by means of a hinge 76 and is normally urged into an open position by means of a coil spring 78 extending around hinge 76. A first CCD 80a is mounted at the distal end of barrel 72 just behind objective optics 82a in the form of an objective lens. Similarly, CCD 80b is mounted in end cap 74 behind objective optics 82b which is in the form of another objective lens for focusing an image of operative site onto the CCD. These CCDs 80a and 80b, respectively, together with their objective lenses 82a and 82b, respectively, are mounted in face-to-face relationship when the end cap is in closed position as shown in FIG. 8. Thus, they lie along the axis 84 of barrel 72, as seen in FIG. 8. A locking rod 88 is mounted for sliding movement through a channel 90 extending within and along the length of barrel 72. Locking rod 88 has a distal end that extends into sleeve 92 in end cap 74 with a frictional fit sufficient to hold end cap 74 in the closed position against the force of coil spring 78.

Electronic packaging 94a is connected to CCD 80a and has a distal end connected to image signal transmitting wires 96 which extend longitudinally through barrel 72. Similarly, CCD 80b is connected to electronic packaging 94 which in turn is connected to image signal transmitting wires 98 which extend past hinge 76 and longitudinally through barrel 72. Also, light transmitting fibers 100 are packed tightly around CCD 80a, objective lens 82a and electronic packaging 94a for providing light to the operative site. These wires and light fibers extend through the proximal end of barrel 72 and are connected in the manner described above with respect to FIGS. 1–3. The mode of operation is identical.

In use, endoscope 70 is inserted to the operative site whereupon locking rod 88 is withdrawn from sleeve 92 so that end cap 74 snaps open to the position shown in FIGS. 7 and 9. This separation of CCDs 80a and 80b, as shown in FIG. 9, creates a parallax wherein CCD 80a lies along axis 84 of barrel 72 and CCD 80b lies along axis 102 of end cap 74.

With this arrangement barrel 72 can be made smaller than either barrels 12 or barrels 52, or alternatively it can be provided with channels 104 and 106, respectively, for introducing fluid or instruments to the operative area.

When it is desired to withdraw the endoscope, the end cap will be pushed to closed position by engagement therewith with the end of a trochar through which the endoscope has been introduced into the body or by engagement with a body passageway through which the endoscope has been introduced to the operative site.

FIGS. 10 and 11 show a conventional electronic chip C. The chip includes one or more interconnect layers, such as layer 110, having a peripheral edge 111, and layer 112, having a peripheral edge 113, through which an image is projected onto a pixel layer 114, having a peripheral edge 115. This layer is supported on a thick silicon base layer 116, having a peripheral edge 121 sized to just fit within and be mounted in an opening 117 in a large substrate 118, having a peripheral edge 119 which defines a first area. The substrate 118 is similar to a picture frame which provides a support for the chip and protects it from damage. This substrate may be made of any one of several materials, such as ceramic or plastic. A plurality of leads 120 connect the electronics in interconnecting layers to electrical contacts 122 on substrate 118. Electrical pins 124 are connected to the substrate and to electrical contacts 122, along the margins, as shown, for connection to electrical wires (not shown) for transmitting electrical information into and out of the chip. It will be noted that the images projected in the direction of arrow 126 as shown in FIG. 10, must be projected through interconnect layers 110 and 112 onto pixel layer 114. Thereby reducing the amount of light that can be transmitted to the pixel layer. The light which does pass through the interconnect layers is distorted by them, resulting in a distorted image being projected onto the pixel layer. Also, since substrate 118 is substantially bigger in area than pixel layer 114, a significantly larger area is required by the chip than the area occupied by the pixel layer and the associated layers above and below it.

By the disclosure of the present invention, an improved CCD of the type shown in FIGS. 12 and 13 is provided. The chip C is removed from substrate 118 and turned over so that silicon layer 116 is at the top. Next, silicon layer 116 is shaved down to a sufficiently thin thickness to allow the transmission of a light image. The desired thickness will vary depending on the particular application. An acceptable thickness range has been found to be between 3 and 200 microns. A preferred range is between 6 and 10 microns. After shaving, a thin layer 130 is formed, having a peripheral edge 131 defining a second area, which is smaller than the first area defined by peripheral edge 119, which is now located above pixel layer 114. After reversing the chip, interconnect layers 110 and 112 are mounted below pixel layer 114, as shown, and posts 132 are indium bump bonded to interconnect layer 110 and extend generally perpendicular thereto within the second area to provide electrical connections for bringing data into and out of the chip. Advantageously, the posts are positioned within the area defined by peripheral edge 115 of pixel layer 114, With this arrangement, the area of modified chip C' is no larger than the area of pixel layer 114, such as 2 mm square.

This allows the modified chip C' to be placed inside an endoscope 134 having a diameter no larger than 3 or 4 mm. The chip is shown near the distal end of endoscope 134, as shown in FIG. 13, with an appropriate lens system 136 for focusing an image on the chip. Because of the thinness of silicon layer 130 and the fact that the light does not need to pass through the interconnect layers 110 and 112, it is possible for pixel layer 114 to receive up to 90% of UV or infrared light in addition to light in the visible light range. Thus, the use of the chip is enhanced for a wider light spectrum thereby increasing its utility. In some applications, filters can be placed over the chip to regulate the frequency of light being utilized by the CCD. In addition, since the light does not have to pass through the interconnect layers, there is less distortion of the image as it is projected onto the pixel layer. Also, a chip constructed in the manner of chip C' can be autoclaved whereas the conventional chip and packaging will be damaged or destroyed by the high temperatures required for autoclaving. Because of the miniaturization of chip C', a pair of such chips can be used in side-by-side relationship within a stereoscopic endoscope without resulting in an endoscope of excessively large diameter. Also, they can be used alone to provide a very miniaturized endoscope, as discussed above, for use in passageways and through trochars in a less intrusive manner than that which was previously possible.

In the foregoing description the pixel layer and interconnect layers have been described as being separate distinct layers, In reality, the elements that make up the chip are stratified as is well understood by those skilled in the art of the construction of CCDs. Therefore, the term "layers" as used herein is intended to cover the pixel layer and interconnect layers in a more integrated and stratified arrangement.

The endoscopes of this invention each may be constructed with fluid impervious construction where optics, fiber optic light fibers, electronic cables are thoroughly sealed against moisture entry into the device so that it may be "soaked" in disinfectant solutions to allow use in surgery. Also the CCDs can be mounted in endoscope made of materials such as glass fibers, optics (objective lenses), an outer enclosure of stainless steel and electronic cables insulated with high temperature plastics such as Teflon or silicone rubber which will also allow the device to be heat sterilized.

The device(s) may be used in endoscopic surgery such as laparoscopy and thoracoscopy and other uses where the body cavity or organ may be under pressure from instilled gases (or fluids). In such case, the operative channel will be "closed" by a suitable stopcock to prevent gas or fluid loss.

Although this device is specifically designed into a small diameter enclosure, it should be understood that it may be used to view structures on the surface of the body or possibly in indirect applications where its small size may not be necessarily required. It may, in this case, be an exoscope or a boroscope.

From the foregoing, the advantages of the present invention are apparent. Stereoscopic endoscope is provided which is of a practical small diameter that can be introduced through body channels or relatively small trochars with minimal discomfort to the patient. Also, when introduced through a trochar, by utilizing a small diameter, the postoperative healing will be enhanced. In one embodiment, the CCDs are mounted transversely across the endoscope in side-by-side relationship. In another embodiment, they are arranged in back-to-back relationship and the image is brought into focus with the CCDs by means of objective optics which includes a prism for changing the direction of the transmitted image. In a third embodiment, a hinged end cap is provided on the endoscope with one CCD being in the barrel of the endoscope and the other being in the end cap. For insertion, the end cap is closed and after the end of the endoscope is positioned at the operative site, the end cap is opened so that the CCDs are arranged in substantially side-by-side relationship and lie along separate axes.

This invention has been described in detail with reference to particular embodiments thereof, but it will be understood that various other modifications can be effected within the spirit and scope of this invention.

I claim:

1. Stereoscopic endoscope comprising:

an elongated thin cylindrical barrel having a distal end and a proximal end;

a pair of miniaturized electronic imaging chips mounted in spaced relationship within said barrel adjacent said distal end thereof, each of said miniaturized electronic imaging chips comprising:

a generally rectangular silicon base layer having a thickness which allows a light image to pass therethrough, said silicon layer having a first side, through which the image is projected, and a second side;

a pixel layer having a first and second side, said first side thereof being attached to said second side of said silicon layer, said pixel layer further having a peripheral edge;

at least one interconnect layer bonded to said second side of said pixel layer; and electrical leads bonded to and extending substantially perpendicular from said interconnect layer within an area defined by said peripheral edge of said pixel layer a pair of objective optics mounted within said barrel between said distal end thereof and the respective chips, having a distal end coterminous with said distal end of said barrel, to focus an image observed through the endoscope on the chips;

image signal transmitting wires connected to said electrical leads and extending longitudinally through said barrel and out said proximal end thereof for transmitting an image signal to a remote location;

light transmitting fibers positioned around said objective optics and said chips and having distal ends coterminous with said distal end of said barrel;

a first connector secured to said proximal end of said wires for connection to a stereoscopic image producing device; and a second connector secured to said proximal end of said light transmitting fibers for connection to a light source.

2. Apparatus, as claimed in claim 1, wherein:

said chips, each face said distal end of said barrel.

3. A stereoscopic endoscope comprising:

a cylindrical barrel having a distal end and a proximal end;

a pair of miniaturized electronic imaging chips mounted in spaced relationship within said barrel adjacent said distal end thereof, each of said chips including:

a silicon base layer having a thickness which allows a light image to pass therethrough, said silicon layer having a first and second side, said first side through which the image is projected;

a pixel layer having a first and second side, said first side thereof being attached to said second side of said silicon layer said pixel layer further having a peripheral edge; and at least one interconnect layer bonded to said second side of said pixel layer; electrical leads bonded to and extending substantially perpendicular from said interconnect layer within an area defined by said peripheral edge of said pixel layer;

a pair of objective optics mounted within said barrel between said distal end thereof and the respective chips, each of said objective optics having a distal end coterminous with said distal end of said barrel to focus an image observed through the endoscope on the chips;

image signal transmitting wires electrically coupled to said electrical leads and extending longitudinally through said barrel and out said proximal end thereof for transmitting an image signal to a remote location; and at least one light transmitting fiber positioned adjacent said objective optics and said chips, said at least one fiber having a distal end coterminous with said distal end of said barrel.

4. Apparatus, as claimed in claim 3, wherein: said chips are arranged in side-by-side relationship and wherein said chips face said distal end of said barrel.

5. Apparatus, as claimed in claim 3, further including:

a pair of prisms mounted within said barrel proximally from said objective optics and adjacent to said chips in corresponding relation thereto, said chips arranged in back-to-back relationship wherein light passes through said objective optics and said prisms and is bent at an angle by said prisms such that each prism reflects light onto the corresponding chip.

6. A stereoscopic endoscope comprising:

a cylindrical barrel having a distal end and a proximal end;

an end cap hinged to said distal end of said barrel so that it is movable between a closed position covering said distal end of said barrel, said end cap having an axis lying along the longitudinal axis of said barrel, and an open position wherein said end cap lies along side said barrel with said axis thereof generally parallel to said barrel axis, said end cap hinged by means of a hinge element having a spring that normally urges said end cap toward said open position;

first objective optics mounted within said barrel at said distal end thereof;

a first imaging chip mounted within said barrel adjacent said first objective optics and positioned to receive an image focused on it by said first objective optics;

first image signal transmitting wires connected to said first imaging chip and extending longitudinally through said barrel and out said promixal end thereof for transmitting a first image signal to a remote location;

at least one light transmitting fiber positioned around said first objective objects and said first imaging chip and having a distal end coterminous with said distal end of said barrel;

second objective optics mounted within said end cap in face-to-face relationship with said first objective lens when said end cap is in said closed position;

a second imaging chip mounted within said end cap adjacent said second objective optics and positioned to receive an image focused on it by said second objective optics;

second image signal transmitting wires connected to said second imaging chip extending from said end cap and longitudinally through said barrel and out said proximate end thereof for transmitting a second image signal to a remote location when said end cap is in said open position with said first and second objective optics in side-by-side relationship to provide stereoscopic images;

said first and second imaging chips each including:

a silicon base layer having a thickness which allows a light image to pass therethrough, said silicon layer having a first and second side, said first side through which the image is projected;

a pixel layer having a first and second side, said first side thereof being attached to said second side of said silicon layer said pixel layer further having a peripheral edge;

at least one interconnect layer bonded to said second side of second pixel layer; and electrical leads bonded to and extending substantially perpendicular from said interconnect layer within an area defined by said peripheral edge of said pixel layer.

7. Apparatus, as claimed in claim 6, further including:

a channel extending longitudinally through said barrel;

a sleeve in said end cap aligned with said channel when said end cap is in said closed position; and a locking rod extendable through said channel and having a distal end receivable in frictional engagement with said sleeve to hold said end cap in said closed position against the force of said spring when said endoscope is inserted into a patient's body.

8. A stereoscopic endoscope comprising:

a cylindrical barrel having a distal end and a promixal end;

an end cap hinged to said distal end of said barrel, said end cap being movable between an open position and a closed position, said end cap having spring means attached thereto for urging said end cap towards said open position;

first objective optics mounted within said barrel at said distal end thereof;

a first imaging chip mounted within said barrel adjacent said first objective optics and positioned to receive an image focused on it by said first objective optics;

first image signal transmitting wires connected to said first imaging chip for transmitting a first image signal to a remote location;

at least one light transmitting fiber position adjacent said first objective optics and said first imaging chip and having distal ends coterminous with said distal end of said barrel;

second objective optics mounted within said end cap;

a second imaging chip mounted within said end cap adjacent said second objective optics and positioned to receive an image focused on it by said second objective optics;

second image signal transmitting wires connected to said second imaging chip for transmitting a second image signal to a remote location; and said first and second imaging chips comprising:

a silicon base layer having a thickness which allows a light image to pass therethrough, said silicon layer having a first side and a second side, said first side through which the image is projected;

a pixel layer having a first and second side, said first side thereof being attached to said second side of said silicon layer said pixel layer further having a peripheral edge;

at least one interconnect layer bonded to said second side of said pixel layer; and electrical leads bonded to and extending substantially perpendicular from said interconnect layer within an area defined by said peripheral edge of said pixel layer.

9. Apparatus, as claimed in claim 8, further including:

a channel extending longitudinally through said barrel;

a sleeve in said end cap aligned with said channel when said end cap is in the closed position; and a locking rod extendable through said channel and having a distal end receivable in said sleeve to hold said end cap in said closed position.

* * * * *